(12) United States Patent
Negiz et al.

(10) Patent No.: US 8,044,253 B2
(45) Date of Patent: Oct. 25, 2011

(54) XYLENE PRODUCTION PROCESSES WITH INTEGRATED FEEDSTOCK TREATMENT

(75) Inventors: Antoine Negiz, Wilmette, IL (US); Edwin P. Boldingh, Arlington Heights, IL (US); James E. Rekoske, Glenview, IL (US); Eric J. Baker, Chicago, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 12/917,045

(22) Filed: Nov. 1, 2010

(65) Prior Publication Data

US 2011/0046427 A1    Feb. 24, 2011

Related U.S. Application Data

(62) Division of application No. 11/830,424, filed on Jul. 30, 2007, now Pat. No. 7,847,137.

(51) Int. Cl.
*C07C 6/12* (2006.01)
*C07C 5/03* (2006.01)
(52) U.S. Cl. .................. 585/475; 585/258; 585/800
(58) Field of Classification Search .............. 585/475, 585/258, 800
See application file for complete search history.

(56) References Cited

U.S. PATENT DOCUMENTS

4,795,550 A * 1/1989 Sachtler et al. .............. 208/307
* cited by examiner

*Primary Examiner* — Thuan Dinh Dang
(74) *Attorney, Agent, or Firm* — David J Piasecki (57) ABSTRACT

A process for aromatic transalkylation and olefin reduction of a feed stream is disclosed. Transalkylation conditions provide a product having increased xylene concentration and reduced olefin concentration relative to the feed. The process may be used in a xylene production facility to minimize or avoid the necessity of feedstock pretreatment such as hydrotreating, hydrogenation, or treating with clay and/or molecular sieves.

19 Claims, 3 Drawing Sheets

XYLENE PRODUCTION PROCESSES WITH INTEGRATED FEEDSTOCK TREATMENT

CROSS-REFERENCE TO RELATED APPLICATION

This application is a Division of U.S. application Ser. No. 11/830,424 which was filed Jul. 30, 2007 now U.S. Pat. No. 7,847,137 and which is incorporated by reference in its entirety

FIELD OF THE INVENTION

This invention pertains to aromatic transalkylation processes. In particular, the olefin content of feedstock can be reduced in the processes of this invention such as the transalkylation of aromatics for the production of xylene. The invention is applicable to eliminate or reduce the need for feedstock pretreatment such as hydrotreating, hydrogenation, and treating with clay and/or molecular sieves in xylene production facilities.

BACKGROUND OF THE INVENTION

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production. The distribution of xylene isomers from catalytic reforming and other sources generally does not match that of the sought isomers for chemical intermediates and thus the producer converts the feedstocks to generate more of the sought isomers.

The production of xylenes is practiced commercially in large-scale facilities and is highly competitive. Concerns exist not only about the effective conversion of feedstock through one or more of isomerization, transalkylation and disproportionation to product xylenes, but also other competitive aspects with respect to such facilities including capital costs and energy costs. A prior art aromatics complex flow scheme has been disclosed by Meyers in part 2 of the Handbook of Petroleum Refining Processes, Second Edition, 1997, published by McGraw-Hill.

Various sources have been proposed for monocyclic aromatics as a feed to a xylene production facility. The most prevalent are the catalytic reforming of naphtha fractions and pyrolysis followed by hydrotreating of naphtha fractions. These processes typically produce a wide spectrum of chemical compounds including not only the sought monocyclic aromatics but also polycyclic aromatics and olefins. Polycyclic aromatics and olefins are typically undesirable impurities in xylene production facilities. They can have a negative impact on the product quality and the efficiency of the processes such as by requiring additional process steps, reducing catalyst life, decreasing stability of the product, and causing undesirable product color. Polycyclic aromatics are typically removed by distillation from the desired monocyclic aromatics. These removed polycyclic aromatics are then disposed of in any suitable manner, usually as a fuel, and thus have lesser value. It is also known that the polycyclic aromatics can be converted to useful monocyclic aromatics such as toluene, xylenes and C9+ monocyclic aromatics The quality of feed streams to the various process units within a xylene production facility is also specified to ensure proper performance. For example, the olefin content of streams fed to some process units of xylene production facilities, including the transalkylation unit, is limited. Thus, olefin are recognized as a contaminant in transalkylation feed and the conventional practice is to reduce the olefin content to an acceptable level (feed specification limit) using various olefin removal processes such as hydrotreating, hydrogenation, and treating with clay and/or molecular sieves. Olefins are for example commonly removed from the xylene production facility feedstock and/or intermediate streams at various locations within the facility by clay treating. In clay treaters, olefins are converted to oligomers which can cause fouling of the clay. The cost to operate clay treaters, including reloading them with fresh clay and disposal of the organic contaminated spent clay, can be a significant financial burden on the commercial-scale producer of xylenes. Moreover, clay treaters can result in alkylation of an olefin to an aromatic ring. Hence, the effluent from a clay treater can contain aromatic rings having C2+ substituents such as ethylbenzene, propylbenzene, and methylethylbenzene. Thus the value of the aromatic feedstock for the production of benzene, toluene and xylene is reduced.

SUMMARY OF THE INVENTION

The invention enables the removal of olefins in a transalkylation process wherein aromatics are reacted to produce xylene. In an embodiment, the invention is a process for transalkylating and removing olefins from a feed stream having a Bromine Index of at least about 50 and comprising an aromatic compound having at least six carbon atoms, said process comprising contacting the feed stream with a transalkylation catalyst comprising an acidic molecular sieve and at least one metal component at transalkylation conditions to provide a transalkylation product having an increased concentration of xylene and a Bromine Index at least 60% lower than the Bromine Index of the feed stream.

In another embodiment, processes are provided for the production of xylene isomers from feedstock comprising olefins and polycyclic aromatics in a Xylene Loop process while enabling reduction in capital and operating costs. Xylene Loop processes are those which comprise separating the Xylene Loop feed by fractional distillation to provide a stream comprising xylenes, subjecting the xylene stream to selective xylene isomer separation, isomerizing an effluent stream from the selective xylene isomer separation to re-equilibrate the xylene isomer concentrations, and recycling an isomerization effluent to the fractional distillation. The apparatus for this fractional distillation is also referred to herein as the xylene column.

In an embodiment of this invention, at least a portion of a feedstock comprising C8 aromatics and olefins is combined with a stream comprising C9+ aromatics, such as, a higher boiling fraction from the xylene column, and the combined stream is subjected to transalkylation conditions sufficient not only to increase the xylene concentration but also to remove olefins and convert polycyclic aromatics to monocyclic aromatics. Thus, the processes of this invention by enabling the use of aromatic feedstocks containing olefins, reduce or eliminate the need for pretreatment such as hydrotreating, hydrogenation, and clay and/or molecular sieve treatment, thereby reducing capital and operating costs.

DETAILED DESCRIPTION OF THE INVENTION

Processes and apparatus for the production of xylene isomers are disclosed, for instance, in Robert A. Meyers, Handbook of Petroleum Refining Processes, Second Edition, McGraw-Hill, 1997, Part 2. In a conventional process, a xylene production facility feedstock comprising C8 aromatics and olefins is fractionated to remove benzene and toluene, then subjected to fractional distillation in a xylene column to provide a C8 aromatic stream from which one or more xylene isomers of interest is recovered. The most sought isomer is para-xylene, although ortho-xylene and meta-xylene do find commercial applications. After separating the sought xylene isomer, the remaining stream is isomerized and recycled to the xylene column which also provides a higher boiling fraction containing $C9^+$ aromatics. The C8 containing feedstock may be fractionated in alternative ways such as separating the $C9^+$ aromatics first followed by removing the $C7^-$ aromatics in the xylene column.

A C8 containing aromatics feedstock to a xylene production facility is typically derived from petroleum processing, e.g., from the catalytic reforming of naphtha fractions or from pyrolysis followed by hydrotreating of naphtha fractions. These processes typically produce a wide spectrum of chemical compounds including aliphatic (saturated and unsaturated) and aromatic (monocyclic and polycyclic) compounds. The feedstock is typically characterized in terms of its Initial Boiling Point and its End Boiling Point. The End Boiling Point is the temperature at which 99.5 mass percent of the sample would have boiled as determined by ASTM Method D2887 simulated distillation GC method. Typically, the End Boiling Point of the xylene production facility feedstock is at least about 210° C. and the feedstock End Boiling Point is at least about 220° C. in another embodiment. In another embodiment the End Boiling Point ranges from about 240° C. to about 280° C. and from about 340° C. to about 360° C. in another embodiment. Thus, the feedstock may contain highly substituted aromatic compounds and polycyclic aromatic compounds. Typically, the feedstock contains aliphatics and lower boiling compounds including aromatics such as benzene and toluene. Often, the feedstock has an Initial Boiling Point of less than about 80° C. and in some embodiments less than about 70° C. Consequently, a feedstock may contain C5 and possibly lighter aliphatics depending upon any pretreatment such as distillation to remove C4 and lower hydrocarbons. A feedstock may be tailored such as by prefractionation to comprise a more select group of components. Also, multiple feedstocks may be provided simultaneously to a xylene production facility.

A xylene production facility feedstock may have the compositions set forth in Table 1.

TABLE 1

| Component | Range, mass-% |
|---|---|
| Aliphatics, C6 and lower | 2-15 |
| Aliphatics, C7 and C8 | 3-10 |
| Aliphatics, above C8 | 0-2 |
| Benzene | 1-10 |
| Toluene | 15-30 |
| C8 aromatics | 25-40 |
| C9 aromatics | 10-15 |
| $C10^+$ aromatics | 1-7 |

Of the $C9^+$ aromatics in the feedstock, about 1 to about 50, often about 3 to about 30, mass percent are polycyclic aromatics. The olefin content of the feedstock and other streams is usually reported as a Bromine Index. Typically the feedstock has a Bromine Index of at least about 100, in some embodiments the Bromine Index is at least about 300 and in other embodiments the Bromine Index is at least about 600.

The Bromine Index is an indicator of the olefin content. The Bromine Index is determined in accordance with the procedure spelled out in UOP Method 304-90, obtainable through ASTM International, 100 Barr Harbor Drive, West Conshohocken, Pa., USA. In accordance with this procedure, a sample is dissolved in a titration solvent containing a catalyst that aids in the titration reaction. The solution is titrated potentiometrically at room temperature with a 0.01 M bromide-bromate solution. The titration uses a platinum indicating and a glass reference electrode in conjunction with a recording potentiometric titrator. The Bromine Index is calculated from the milligrams of bromine consumed per 100 g of the sample under the test conditions. It should be pointed out that there are at least three other standard test methods for Bromine Index, including ASTM D 1492, "Bromine Index of Aromatic Hydrocarbons by Coulometric Titration"; ASTM D 5776, "Bromine Index of Aromatic Hydrocarbons by Electrometric Titration"; and ASTM D 2710, "Bromine Index of Petroleum Hydrocarbons by Electrometric Titration". Information on these ASTM methods is also available from ASTM International. UOP Method 304-90 is not equivalent to each of these or other methods of measuring Bromine Index; therefore, it is to be understood that the numerical values of Bromine Index herein are as measured by UOP Method 304-90 only.

To provide a suitable feed stream to the Xylene Loop, the xylene production facility feedstock comprising olefins and C8 aromatics needs to undergo treatment to reduce its olefin content. In accordance with an embodiment of this invention, the C8 aromatics containing feedstock is mixed with a $C9^+$ aromatics stream, which is preferably, the higher boiling fraction containing $C9^+$ aromatics from the xylene column. This mixture is subjected to transalkylation conditions to provide a transalkylation product having a greater amount of xylenes and a reduced Bromine Index. The mass ratio of the C8 aromatics containing feedstock to the $C9^+$ aromatics stream in the mixture can vary widely. Often this ratio is between about 0.01:1 to about 3:1 or more. In some embodiments, this ratio is between about 0.1:1 to about 2:1, and in other embodiments it is between about 0.3:1 to about 1.2:1. The mixture will usually have a lower concentration of xylenes than the feedstock; often less than about 35 mass percent of the total aromatics in the mixture are xylenes. In another embodiment, less than about 30 mass percent of the total aromatics in the mixture are xylenes, and in other embodiments between about 5 and about 25 mass percent of the total aromatics in the mixture are xylenes. Where lighter aromatics (benzene and/or toluene) are present in mixture, the molar ratio of (benzene plus toluene) to $C9^+$ aromatics in the mixture is greater than about 0.01:1 in an embodiment. In another embodiment, the (benzene plus toluene) to C9+ aromatics ratio is greater than about 0.5:1 and in an embodiment this ratio is between about 0.5:1 and about 2:1.

Thus, a transalkylation process of this invention may be used to produce xylenes and reduce the olefin content of a feed. As used herein, the term transalkylation encompasses transalkylation between and among alkyl aromatics, between benzene and alkyl aromatics, between benzene and alkyl naphthenic compounds such as methylcyclopentane and methylcyclohexane, and it includes disproportionation, e.g., of toluene to benzene and xylene. Thus, in an embodiment, the transalkylation feed comprises an aromatic compound having at least six carbon atoms. The transalkylation processes of this invention can process a feed having a Bromine Index of at least about 50. In an embodiment, the Bromine Index of the transalkylation feed is at least about 100, in another embodiment it is at least about 300, and in an embodiment the Bromine Index of the transalkylation feed is at least about 500. The transalkylation conditions are sufficient to provide a transalkylation product having a higher concentration of xylenes than the transalkylation feed and a Bromine Index that is at least 60% lower than the Bromine Index of the transalkylation feed. In some embodiments, the Bromine Index of the product is at least 80% lower than that of the feed. In an embodiment the Bromine Index of the product is less than about 30 when the Bromine Index of the feed is at least about 200. In an embodiment, the Bromine Index of the product is less than about 20. In another embodiment the Bromine Index of the product is less than about 10. The transalkylation process may be part of a xylene production complex, another arrangement of process units, or it may be a stand alone unit. The aromatic composition of the transalkylation feed may vary considerably. The transalkylation feed comprises an aromatic compound having at least six carbon atoms. In an embodiment, the transalkylation feed comprises at least one of toluene and C9+ aromatics. The feed may optionally include one or both of benzene and C8 aromatics. In an embodiment, the transalkylation feed comprises C9+ aromatics and at least one of benzene and toluene. In an embodiment, the transalkylation feed End Boiling Point is at least about 190° C. In another embodiment, the transalkylation feed End Boiling Point is at least about 220° C., and at least 240° C. in another embodiment. In an embodiment, the transalkylation feed End Boiling Point is between about 240° C. and about 280° C. and in another embodiment between about 340° C. and about 360° C.

The specific transalkylation conditions will, in part, be dependent upon the catalyst and its activity as well as the composition of the transalkylation feed. In general, the transalkylation conditions comprise elevated temperature, e.g., from about 100° C. to about 425° C., preferably, from about 200° C. to about 400° C. In commercial facilities, the transalkylation temperature is often increased to compensate for any decreasing activity of the catalyst. The feed to a transalkylation reactor usually first is heated by indirect heat exchange against the effluent of the reactor and then is heated to reaction temperature by exchange with a warmer stream, steam or a furnace. The feed then is passed through a reaction zone, which may comprise one or more individual reactors containing catalyst of this invention. The reactors may be of any suitable type and configuration. The use of a single reaction vessel having a fixed cylindrical bed of catalyst is preferred, but other reaction configurations utilizing moving beds of catalyst or radial-flow reactors may be employed if desired. Transalkylation conditions include pressures ranging from about 100 kPa to about 10 MPa (absolute), preferably from about 0.5 MPa to about 5 MPa (absolute). The transalkylation reaction can be effected over a wide range of space velocities. The weight hourly space velocity (WHSV) generally is in the range of from about 0.1 $hr^{-1}$ to about 30 $hr^{-1}$ preferably from about 0.5 $hr^{-1}$ to about 20 $hr^{-1}$, and most often between about 1 $hr^{-1}$ to about 5 $hr^{-1}$.

By this invention, it has been found that various combinations of the transalkylation conditions or operating parameters including the catalyst can provide the desired reduction of olefins in the transalkylation feed without undue aromatic Ring Loss while still achieving transalkylation to increase xylene concentration. Preferred combinations of transalkylation conditions are those under which the net make of methane is less than about 0.5 mass percent. In an embodiment, the net make of methane is less than about 0.2 mass percent. The net make of methane is the increase in methane concentration from that in the feed to that in the product. Preferably, the Ring Loss, which is the mole percent loss of monocyclic aromatic rings in the product as compared to that of the feed, is less than about 2 mole percent. In an embodiment, the Ring Loss is less than about 1.5 mole percent.

Transalkylation can be conducted in the vapor phase and in the presence of hydrogen or in the liquid phase. For liquid phase transalkylation, the adding of hydrogen is optional but preferred. If the feed is transalkylated in the gas phase, then hydrogen is added, commonly in an amount of from about 0.1 moles per mole of hydrocarbon up to 10 moles per mole of hydrocarbon in the mixture fed to the transalkylation unit. This operating parameter is referred to as the hydrogen to hydrocarbon ratio and is frequently expressed for example as 5.5$H_2$/HC, that is 5.5 moles of hydrogen per mole of hydrocarbon. If the transalkylation is conducted in the liquid phase, it may be done in a substantial absence of hydrogen beyond what may already be present and dissolved in a typical liquid aromatics feedstock. In the case of partial liquid phase, hydrogen may be added in an amount less than 1 mole per mole of hydrocarbons. Preferably, the hydrogen to hydrocarbon ratio in the liquid, partial liquid, or gas phase transalkylation modes is at least about 1.5$H_2$/HC. In an embodiment, it is at least about 2$H_2$/HC, between about 2$H_2$/HC and about 8$H_2$/HC in another embodiment.

The transalkylation process provides xylenes and thus the transalkylation product contains a higher concentration of xylenes relative to the feed. When lighter aromatics (benzene and toluene) are included in the feed, the molar ratio of lighter aromatics to C9+ aromatics in the feed is greater than about 0.01:1 and in an embodiment this ratio is between about 0.1:1 and about 10:1. In another embodiment, this molar ratio of (benzene plus toluene) to C9+ aromatics in the feed is between about 0.9:1 to about 5:1.

In an embodiment, the transalkylation feed comprises at least about 1 mass percent polycyclic aromatics. During transalkylation, polycyclic aromatics are converted, to a significant degree. In an embodiment, at least about 50 mole percent of the polycyclic aromatics are converted to monocyclic aromatics. Hence, it is possible, in accordance with an aspect of this invention, to convert indanes and naphthalenes, whether or not alkyl substituted, into alkyl substituted monocyclic aromatics. The degradation products of indane and naphthalene during the conversion to monocyclic aromatics can provide a source of alkyl moieties. Significantly, the processes of this invention enable the conversion of polycyclic aromatics to monocyclic aromatics without undue loss of the monocyclic moieties thus providing high selectivity to the sought monocyclic alkyl aromatics.

In an embodiment, transalkylation is conducted for a time and under other conditions sufficient that at least about 10 mole percent of the heavier alkyl aromatics (C9+) are consumed. In an embodiment, at least about 20 mole percent of the heavier alkyl aromatics are consumed and in another embodiment between about 20 and about 90 mole percent of the heavier alkyl aromatics are consumed. At least about 70 mole percent of the heavier alkyl aromatics consumed are converted to lower molecular weight aromatics in an embodiment. In another embodiment, at least about 75 mole percent of the heavier alkyl aromatics consumed are converted to lower molecular weight aromatics. The transalkylation conditions are preferably sufficient to provide a transalkylation product having an End Boiling Point at least about 5° C. lower than that of the transalkylation feed. In another embodiment, the transalkylation product has an End Boiling Point at least about 10° C. lower than that of the transalkylation feed.

The transalkylation conditions include the presence of transalkylation catalyst comprising a metal component and an acidic molecular sieve component. In an embodiment, the catalyst comprises an acidic molecular sieve component, a metal component, and an inorganic oxide component. The metal component typically has hydrogenation functionality. The metal component comprises at least one of a noble metal and a base metal. The noble metal is a platinum group metal and is selected from the group consisting of platinum, palladium, rhodium, ruthenium, osmium, iridium and mixtures thereof. The base metal is selected from the group consisting of rhenium, tin, germanium, lead, iron, cobalt, nickel, indium, gallium, zinc, uranium, dysprosium, thallium, and mixtures thereof. A promoter or modifier may also be used in the catalyst formulation. Such promoters or modifiers are one or more of base metals, IUPAC groups 1, 2, 5, 6, 7, 11, 12, 13, 14, 15, 16 and 17. In an embodiment, the metal component comprises platinum and tin. In another embodiment the metal component comprises rhenium.

A stabilizing amount of metal component reduces the adverse effect of polycyclic aromatics on the catalyst activity. That is, it enhances the catalyst stability. In an embodiment, the rate of deactivation of the catalyst is less than about 200, and in other embodiments less than about 150 percent of that observed with the same catalyst under substantially the same conditions except that the transalkylation feed contains less than about 0.5 mass percent $C11^+$ aromatics. Deactivation is measured as the temperature increase required to maintain constant aromatic conversion under otherwise constant conditions. The rate of deactivation should be determined after the catalyst has lined out, e.g., after about 100 hours of operation. As it is impractical to conduct comparative tests in commercial facilities, preferably the stability determination is conducted in a pilot plant using synthesized feeds.

For purposes of determining whether the catalyst contains a stabilizing amount of metal component, Evaluation Conditions can conveniently be used. Evaluation Conditions are used for catalyst evaluation only and are not necessarily representative of the transalkylation conditions used in accordance with this invention. Evaluation Conditions involve the operation of a pilot plant at a weight hourly space velocity of 1.6 hr-1, pressure of 2760 KPa (gauge), at a hydrogen to hydrocarbon ratio of 6:1, and a weight average bed temperature sufficient to convert about 45 mole percent of the aromatics in the aromatic containing feed. Suitable polycyclic aromatic feeds for Evaluation Conditions fall in the following ranges given in Table 2.

TABLE 2

| Feed Component | Polycyclic Feed, mol-% |
|---|---|
| Toluene | 28-32 |
| C9 monocyclic aromatics | 55-60 |
| C10 monocyclic aromatics | 5-7 |
| Indane | 0.3-0.7 |
| Naphthalene | 0.25-0.4 |
| $C11^+$ aromatics | 4-7 |

For the reference feed, the polycyclic aromatic feed (not including the toluene) is distilled to contain less than about 0.5 mole percent $C11^+$ aromatics and then toluene is added to keep the same toluene to $C9^+$ aromatics mole ratio. The $C11^+$ aromatics include both monocyclic and polycyclic aromatics.

In advantageous catalysts for use in the processes of this invention, the amount of metal component is below that which causes undue aromatic Ring Loss. Under Evaluation Conditions, the Ring Loss is preferably less than about 2 mole percent based upon the total moles of monocyclic aromatic compounds in the feed. Suitable metal amounts in the transalkylation catalyst will depend upon the metal or metals present as well as any promoters or modifiers. In an embodiment, the amount of metal component is in the range from about 0.01 to about 10 mass-percent of the catalyst. In another embodiment the amount of metal component is in the range from about 0.1 to about 3 mass-percent; and in another embodiment, it is in the range from about 0.1 to about 1 mass-percent of the catalyst.

The acidic molecular sieve component comprises one or more molecular sieves. Molecular sieves include, but are not limited to, BEA, MTW, FAU (including zeolite Y, both cubic and hexagonal forms, and zeolite X), MOR, LTL, ITH, ITW, MEL, FER, TON, IWW, MFI, EUO, MTT, HEU, MFS, CHA, ERI, and LTA. Molecular sieves of known structure types have been classified according to their three-letter designation by the Structure Commission of the International Zeolite Association (available at the web site www.iza-structure.org/databases) and such codes are used herein. In an embodiment, the acidic molecular sieve component comprises at least one of MOR and MFI. The molecular sieve component is preferably at least partially in the hydrogen form in the finished catalyst. The acidity of the molecular sieve may be that of the molecular sieve to be used in making the catalyst of the invention or may be achieved during the preparation of the catalyst. In an embodiment, the acidic molecular sieve component has a Total Acidity of at least about 0.15 as determined by Ammonia Temperature Programmed Desorption (Ammonia TPD). In an embodiment, the Total Acidity of the molecular sieve component is at least about 0.25; in another embodiment, the Total Acidity of the molecular sieve component is at least about 0.4; and in another embodiment, the molecular sieve component has a Total Acidity within the range from about 0.4 to about 0.8.

Ammonia TPD involves first heating a sample (about 250 milligrams) of molecular sieve at a rate of about 5° C. per minute to a temperature of about 550° C. in the presence of a 20 volume percent oxygen in helium atmosphere (flow rate of about 100 milliliters per minute). After a hold of about one hour, helium is used to flush the system (about 15 minutes) and the sample is cooled to about 150° C. The sample is then saturated with pulses of ammonia in helium at about 40 milliliters per minute. The total amount of ammonia used is greatly in excess of the amount required to saturate all the acid sites on the sample. The sample is purged with helium (about 40 milliliters per minute) for about 8 hours to remove physisorbed ammonia. With the helium purge continuing, the temperature is increased at a rate of about 10° C. per minute to a final temperature of 600° C. The amount of ammonia desorbed is monitored using a calibrated thermal conductivity detector. The total amount of ammonia is found by integration. Dividing the total amount of ammonia by the dry weight of the molecular sieve sample yields the Total Acidity. As used herein, values of Total Acidity are given in units of millimoles of ammonia per gram of dry molecular sieve.

Where mordenite is a component of the catalyst, the mordenite preferably has a Si/Al2 molar ratio of less than about 40:1. The Si/Al2 molar ratio of mordenite in an embodiment is less than about 25:1, and in another embodiment the mordenite Si/Al2 molar ratio is between about 15:1 and about 25:1. Mordenite may be synthesized with a Si/Al2 molar ratio of between about 10:1 and about 20:1. Such mordenite may be used as synthesized or may be dealuminated before or after incorporation in the catalyst.

MFI molecular sieves used in the catalysts of this invention preferably have a Si/Al2 molar ratio of less than about 80. The Si/Al2 molar ratio of MFI in an embodiment is less than about 40:1 and in another embodiment it is less than about 25:1. In an embodiment the MFI Si/Al2 molar ratio is between about 15:1 and 25:1. The MFI may be used as synthesized or may be dealuminated. Where dealuminated, the activity of the catalyst is enhanced; however, excessive dealumination may result in the transalkylation product containing more components that co-boil with benzene. While not wishing to be limited by theory, the dealumination may cause some mesoporosity to be introduced into the MFI structure. It is believed that the mesoporosity in the MFI structure can enhance overall conversion.

Dealumination may be effected by any suitable technique such as acid treatment and/or steaming. Where steamed molecular sieve is used, it is preferably mildly steamed, e.g., using between about 2 and about 50, preferably between about 5 to about 30, volume percent steam, pressure of from about 100 kPa to about 2 MPa, and temperature of less than about 650° C.; for example, about 500° C. to about 600° C., more preferably about 550° C. to 600° C. The steam calcination may occur before or after the molecular sieve is shaped into the sought catalyst form. Desirable catalysts have been obtained when the steaming occurs after the formation of the catalyst.

In an embodiment, the acidic molecular sieve component comprises MOR and MFI. In an embodiment, the mass ratio of MFI to mordenite is in the range from about 1:10 to about 5:1, and from about 1:10 to about 1:1 in another embodiment. Preferably, the mordenite is at least partially in the hydrogen form in the finished catalyst. In an embodiment the catalyst comprises rhenium, with or without other metal components. See, for instance, co-pending patent applications 60/825,306 and 60/825,313, both filed on Sep. 12, 2006, both of which are herein incorporated by reference in their entireties.

A suitable inorganic oxide component (refractory binder or matrix) is preferably used to facilitate fabrication of the catalyst, provide strength and reduce fabrication costs. Suitable binders include inorganic oxides such as one or more of alumina, magnesia, zirconia, chromia, titania, boria, thoria, aluminum phosphate, and zinc oxide. The preferred inorganic oxide binders include alumina, especially transition and gamma aluminas. Particularly useful aluminas are commercially available under the trade names CATAPAL B and VERSAL 250. In an embodiment, the molecular sieve component is present in a range from about 5 to about 99 mass percent of the catalyst and the refractory inorganic oxide may, when used, be present in a range of from about 1 to about 95 mass percent of the catalyst.

Processing techniques for making the catalyst can affect catalyst performance. For instance, occlusion of catalytically-active sites can occur. Hence, care should be taken that the activity of the catalyst is not unduly impaired. The metal component may be incorporated into the catalyst in any suitable manner such as comulling, coprecipitation or cogellation with the carrier material, ion exchange, or impregnation. This component may exist within the final catalytic composite as a compound such as an oxide, sulfide, halide, or oxyhalide, in chemical combination with one or more of the other ingredients of the composite, or as an elemental metal. One method of preparing the catalyst involves the use of a water-soluble or solvent-soluble, decomposable compound of the metal to impregnate the molecular sieve-containing support. Alternatively, a metal compound may be added at the time of compositing the molecular sieve component and binder. Another method for preparing the catalyst comprises co-mulling the molecular sieve component, metal component and binder to provide an extrudable mixture for forming the sought catalyst shape. One shape of the catalyst of the present invention is a cylinder. Such cylinders can be formed using extrusion methods known to the art. Another shape of the catalyst is one having a trilobal or three-leaf clover type of cross section that can be formed by extrusion. Another shape is a sphere that can be formed using oil-dropping methods or other forming methods known to the art.

Preferably, the catalyst preparation includes at least one oxidation or calcination, step, especially where the metal is rhenium. The oxidation step typically takes place at a temperature of from about 370° C. to about 650° C. An oxygen atmosphere is employed typically comprising air. Generally, the oxidation step will be carried out for a period of time required to convert substantially all of the metallic components to their corresponding oxide form, which is usually from about 0.5 to about 10 hours or more. This time will, of course, vary with the metal component used to make the catalyst, the oxidation temperature employed and the oxygen content of the atmosphere employed. Sometimes steam is present during the calcination, e.g., in an amount of between about 5 and 70, for example, between about 5 and 40 volume percent.

Where a rhenium containing catalyst is used, the catalyst is preferably sulfided. The rhenium is preferably in at least a partial oxide form at the time of sulfiding. In some embodiments, the catalyst is partially reduced prior to or during sulfiding. The amount of reduction is a function of the reducing atmosphere, the temperature of the reduction and the duration of the reduction. Under excessive reducing conditions, especially those involving higher temperature, the dispersion of rhenium in the catalyst can be adversely affected. Where a reduction precedes sulfiding, the reducing temperature preferably less than about 400° C., and in an embodiment in the range from about 100° C. to about 350° C. The duration of the reduction is preferably such that undue agglomeration of the rhenium on the catalyst does not occur and, preferably, such that the rhenium has an oxidation state of at least about +4. Thus, the reduction is typically conducted for a period of less than about 24 hours, with shorter periods being used at higher temperatures. In an embodiment the reduction is conducted at 280° C. for no more than about 12 hours; in another embodiment for 5 to 6 hours at 280° C.

The sulfiding may occur simultaneously with at least a portion of the reduction or subsequent to the reduction. Preferably the reduction takes place in a substantially water-free environment. Preferably, the reducing gas is substantially pure, dry hydrogen (i.e., less than 20 wt-ppm water). However, other gases may be present such as hydrocarbon, CO, nitrogen, etc. The reduction step may be performed under atmospheric pressure or at higher pressures. The preferred pressures are from about 50 kPa (absolute) to about 10 MKa (absolute), and in an embodiment, the pressure is in the range from about 200 to about 5000 kPa (absolute).

The sulfur component may be incorporated into the catalyst by any known technique. Any one or a combination of in situ and/or ex situ sulfur treatment methods may be used. Effective treatment is accomplished by contacting the catalyst with a source of sulfur at a temperature ranging from about 0° C. to about 500° C. The source of sulfur can be contacted with the catalyst directly or via a carrier gas, for example, hydrogen or nitrogen. In an embodiment, the source of sulfur is hydrogen sulfide. Other sources of sulfur may be used, Examples include carbon disulfide and alkylsulfides such as methylsulfide, dimethylsulfide, dimethyldisulfide, diethylsulfide and dibutylsulfide. Preferably catalysts are sulfided in the presence of carbenium ions. As carbenium ions are intermediate chemical reaction products, the most convenient mode of introducing carbenium ions is to effect hydrocarbon cracking during the sulfiding. The hydrocarbon may be any suitable compound capable of being cracked at the sulfiding conditions, and in an embodiment, the hydrocarbons comprises at least one of ethylbenzene, methylethylbenzene and propylbenzene. The acidic molecular sieve component aids in generating carbenium ions. In an embodiment, sulfiding is conducted in the range from about 250° C. to about 500° C., and from about 250° C. to about 400° C. in another embodiment. Where a rhenium containing catalyst has insufficient cracking activity, higher temperatures may be required.

In an embodiment, the sulfiding is accomplished by passing a gas comprising sulfur over the catalyst at a weight hourly space velocity of at least about 0.5 hr-1. The catalyst composition can also be sulfided in situ where a source of sulfur is contacted with the catalyst composition by adding it to the hydrocarbon feed stream in a concentration ranging from about 1 to about 5,000 or 10,000, preferably from about 5 to 500 ppm-volume, sulfur. The need to add a sulfur source to the hydrocarbon feed stream may be reduced or eliminated entirely depending on the actual content of sulfur which may already be present in some hydrocarbon streams.

Depending upon the concentration of the sulfur in the feed, the sulfiding may be accomplished in less than one hour or may be over a longer period of time, e.g., for a day or more. The sulfur treatment may be monitored by measuring the concentration of sulfur in the product off gas. The time calculated for sulfur treatment will depend on the actual concentration of sulfur in the feed and the desired sulfur loading to be achieved on the catalyst. In some instances it has been found that even when more sulfur is provided than sought for the targeted sulfur to rhenium atomic ratio, the sulfur to rhenium ratio appears to reach a level and the rhenium does not become oversulfided.

The sulfiding is typically accomplished such that about 0.2 to about 0.7 atoms of sulfur are provided per atom of rhenium, in another embodiment, about 0.25 to about 0.5 atoms of sulfur are provided per atom of rhenium. Where the catalyst comprises other components that can sorb or react with sulfur, the total amount of sulfur provided should be sufficient to assure that the sought amount of sulfur for the rhenium is provided.

The catalysts may be regenerated by calcination. Regeneration conditions generally comprise the controlled carbon burn-off of carbonaceous deposits on the catalyst in an oxygen containing atmosphere, e.g., air or air with additional nitrogen and/or steam, at temperatures ranging from about 370° C. to about 650° C. for a period of between about 0.5 and about 24 hours.

Thus, in an embodiment the invention is a process for transalkylating and removing olefins from a feedstock comprising C8 aromatics and having a Bromine Index of at least about 100, wherein the feedstock and a stream comprising $C9^+$ aromatics are mixed to have a Bromine Index of at least about 50 and an End Boiling Point of at least about 210° C. This mixture is contacted with a transalkylation catalyst comprising an acidic molecular sieve and at least one metal component at transalkylation conditions to provide a transalkylation product having an increased concentration of xylenes and a Bromine Index at least 60% lower than the Bromine Index of the mixture.

The transalkylation process may be integrated with other processes in a variety of flow schemes. In an embodiment, the transalkylated product is passed to a xylene distillation column, as Xylene Loop feed. At least one desired xylene isomer is recovered from the xylene column product stream comprising xylenes in the xylene isomer separation assembly. The non-equilibrium xylene isomer stream produced by the xylene isomer separation assembly is passed to the xylene isomerization zone which produces an isomerization product having a distribution of xylene isomers closer to equilibrium. The isomerization product is recycled to the xylene column. Under isomerization conditions other reactions can occur such as transalkylation and cracking Hence, isomerization can be a source of higher molecular weight aromatics, and these $C9^+$ aromatics would also be contained in the heavier aromatic-containing fraction from the xylene column.

In some embodiments, a purge is taken from the heavier aromatics containing fraction from the xylene column to prevent any undue build-up of polycyclic aromatics. The purge may be used in any suitable manner, and may, if desired, be used as fuel. Alternatively, the purge is subjected to a separation by distillation to recover C9 and C10 aromatics which can be used as a by-product or passed to the transalkylation assembly.

DETAILED DESCRIPTION OF THE DRAWINGS

Figure 1:
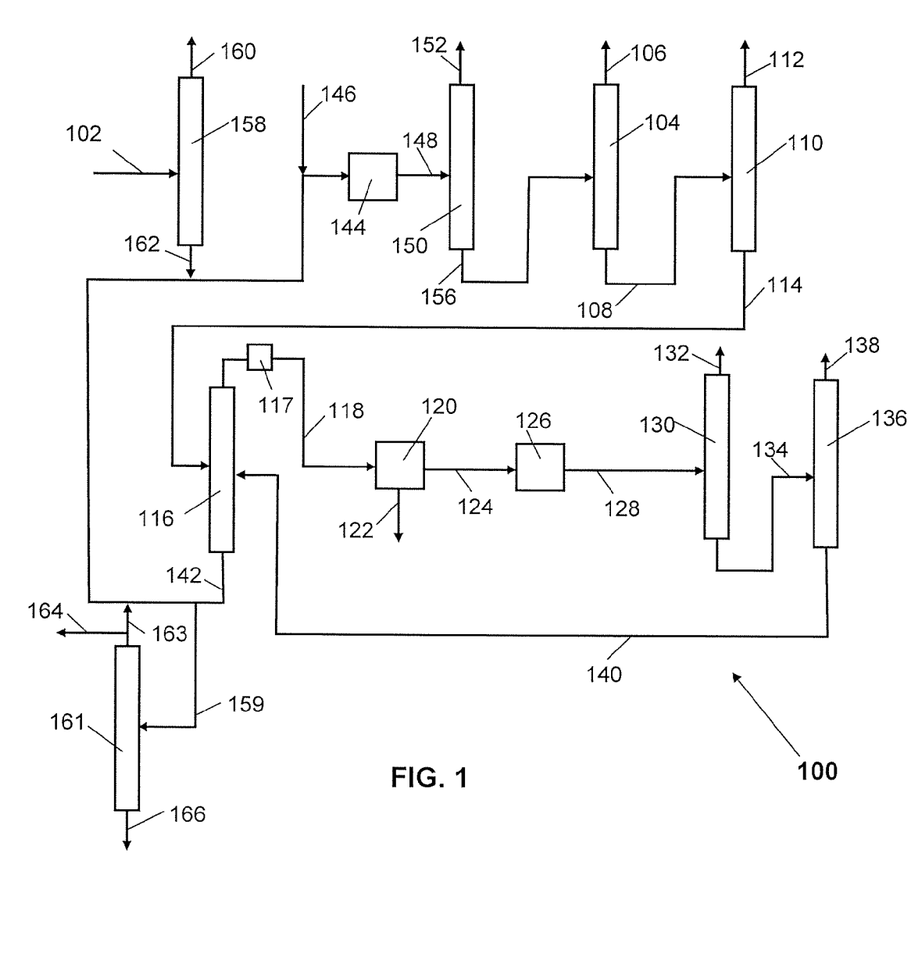
FIG. 1 is a schematic depiction of an apparatus for practicing a process in accordance with this invention.

The invention will be further discussed in connection with FIG. 1 schematically depicting a xylene production apparatus 100. The apparatus depicted is not in limitation of the breadth of the processes of this invention but is intended to assist in the understanding of the principles of the invention.

A feedstock comprising C8 aromatic compounds and olefins is provided to the xylene production apparatus via line 102. The feedstock may be derived from any suitable source. The feedstock may also provide a significant portion of the lighter aromatics (benzene and toluene) useful for transalkylation of $C9^+$ aromatics in the combined stream. In the embodiment shown, the feedstock is passed to feed distillation apparatus 158 to provide by fractional distillation a $C4^-$ hydrocarbons stream. The bottoms stream from feed column 158 is passed via line 162 for combination in line 142 with a portion of the higher boiling fraction from a xylene column to be discussed below. The combination of the streams may be in line 142 as shown or may occur in transalkylation reactor 144. In some embodiments, the C8 aromatics containing feedstock and feed column bottoms further comprises lighter aromatics (benzene and/or toluene) which results in operational savings in that the amount of benzene and/or toluene recovered by distillation for recycle to the transalkylation zone can be reduced or even eliminated. Advantageously, the feed column bottoms stream comprising C8 aromatics and olefins may pass directly to the transalkylation zone. By "direct" it is intended that the transalkylation feed is not subjected to an olefin removal step such as hydrotreating, hydrogenation, or treating with clay and/or molecular sieves prior to transalkylation. However, the transalkylation feed may be subjected to other treatment such as drying if necessary to meet other feed specifications. Likewise, a tailored feedstock to the xylene production apparatus 100 comprising olefins and an aromatic compound having at least six carbon atoms may by-pass the feed column and pass directly to the transalkylation zone without being processed in an olefin removal zone. That is, as is well known in the art, feedstock to a xylene production apparatus may be prepared such as by fractionation, non-aromatics removal, and other processing or treating steps prior to introduction to the apparatus 100 which may obviate the need for feed distillation apparatus 158. Also, as is well known, feed distillation apparatus 158 may produce a variety of effluent streams such as by side cuts, and/or use of multiple columns as exemplified hereinafter. Illustrative, non-limiting, examples of such effluent streams or "cuts" include those enriched in light ends, benzene, toluene, C8 aromatics, and $C9^+$ aromatics.

The resulting mixture is passed to transalkylation zone. As discussed below, the transalkylation zone encompasses various configurations; therefore, it is more generally referred to as the reaction zone 144. Additional lighter aromatic (benzene and/or toluene) can be added to the mixture via line 146. The benzene and toluene may be derived from any suitable source, e.g., from another feed stream to the xylene production facility and/or from lines 106, 112, 132, and 138 as discussed below. The feedstock may also provide a significant portion of the lighter aromatics (benzene and toluene) useful for transalkylation of $C9^+$ aromatics in the combined stream. The transalkylation reactor may comprise one or more individual reactors containing catalyst of this invention. The reactors may be of any suitable type and configuration. The use of a single reaction vessel having a fixed cylindrical bed of catalyst is preferred, but other reaction configurations utilizing moving beds of catalyst or radial flow reactors may be employed if desired.

As stated above, the transalkylation in accordance with the processes of this invention provides a transalkylation product containing an increased concentration of xylenes and a reduced concentration of olefins. Thus, the reaction zone comprises at least one inlet for receiving the xylene production facility feedstock either directly or directly after fractionation in the feed column, that is, without transalkylation feed passing through an olefin removal zone. The transalkylation or reaction zone product is discharged from the reaction zone outlet to the reaction zone product distillation assembly which separates the reaction zone product into various streams for recycle within the xylene production facility and/ or for discharge as products. In the embodiment shown, the reaction zone product distillation assembly comprises the stripper 150, benzene 104, and toluene 110 columns. The transalkylation or reaction zone product is passed via line 148 to stripper column 150 to remove lights separated by fractional distillation via line 152. Stripper column 150 also provides a higher boiling $C6^+$ fraction which is passed to benzene column 104. Benzene column 104 effects by fractional distillation the separation of benzene, recovered as overhead in line 106, from $C7^+$ aromatics recovered as a bottoms fraction. The bottoms fraction from benzene column 104 is passed via line 108 to toluene column 110. In toluene column 110 fractional distillation provides a toluene overhead that is removed via line 112 and a $C8^+$ aromatics bottoms fraction that is passed via line 114 to xylene column 116.

In an embodiment not illustrated, toluene may be converted to xylenes and benzene in an optional toluene disproportionation reaction zone. Whether to use a toluene disproportionation unit operation is dependent upon the feeds and the economics for a given facility. Disproportionation is effected through a catalytic reaction and any of such processes known in the art may be used in conjunction with this invention. Preferred disproportionation conditions to increase the para-xylene produced include precoked catalysts as described in U.S. Pat. No. 6,429,347 incorporated herein by reference in its entirety.

Xylene column 116 separates by fractional distillation a lower boiling C8 aromatics stream containing at least two xylene isomers. In another embodiment, the xylene column effluent stream comprising C8 aromatics is a higher boiling product stream. One or more xylene isomers are recovered from this C8 aromatics stream. If ortho-xylene is the sought isomer, the separation is usually effected by fractional distillation. The para-xylene isomer may be recovered by selective crystallization fractionation or selective adsorption such as a simulated moving bed adsorptive separation. Meta-xylene recovery by sorption processes is also known. Xylene isomer separation processes are well known to those of ordinary skill in the art and any known process may be used individually or in combination to obtain the one or more sought isomers. Thus, this C8 aromatics stream passes from a first outlet of xylene column 116 to an inlet of selective xylene isomer separation assembly 120 via line 118.

Olefin removal apparatus 117 is optionally provided in line 118 to remove any olefins. By the processes of this invention, the transalkylation removes virtually all olefins from the xylene production facility feedstock. Hence, the lower boiling C8 aromatics stream in line 118 will contain only the little amount of olefins produced in the Xylene Loop, e.g., by isomerization, and that residual amount contained in the transalkylation product. In some embodiments where olefin production in the isomerization zone is slight, olefin removal apparatus 117 may be eliminated entirely. In other embodiments such as when the xylene isomerization zone produces higher levels of olefins removal apparatus 117 may be required. Even so, olefin removal apparatus 117 can be relatively small and have a long service life, thereby resulting in capital and operating cost savings. Moreover, an olefin removal zone may need only to be positioned in one location within the production apparatus 100, preferably to treat the C8 aromatics stream passing from the xylene column outlet. In this embodiment, selective xylene isomer separation unit 120 is a selective sorption unit and para-xylene is withdrawn through a first outlet and via line 122. The non-equilibrium isomer stream, depleted in para-xylene, also referred to as the raffinate, is passed from xylene separator 120 through a second outlet to isomerization zone 126 via line 124.

The xylene isomerization serves to re-equilibrate the non-equilibrium mixture of xylenes. For instance, where para-xylene is the sought product and is removed, additional para-xylene is produced by reestablishing an equilibrium or near-equilibrium distribution of xylene isomers. Any ethylbenzene in the para-xylene separation unit raffinate is either converted to additional xylenes or converted to benzene by dealkylation, depending upon the type of isomerization catalyst used and other conditions. In an embodiment, conversion of ethylbenzene by dealkylation is favored to reduce complexities in handling larger quantities of naphthenes that typically are involved in the ethylbenzene conversion to xylenes. In one such embodiment, the total naphthenes in the feed to isomerization reactor 126 is less than about 1, preferably less than about 0.7, mass percent. Conditions that favor isomerization of ethylbenzene include the presence of hydrogen in a mole ratio to hydrocarbon of at least about 0.1:1, for example, from about 0.5:1 to about 6:1, preferably from about 1.5:1 to about 5:1. Preferably the feed stream contains naphthenes, and more preferably a sufficient concentration of naphthenes is provided in the feed stream to enhance the conversion of ethylbenzene, e.g., between about 2 and 20 mass-percent naphthenes. Preferably, the isomerization is conducted under at least partially vapor phase conditions. The isomerization section may include a hydrogenation unit operation followed by a dehydrogenation unit operation.

Xylene isomerization involves the use of isomerization catalyst under isomerization conditions to provide an isomerate. The isomerization catalyst is typically composed of a molecular sieve component, a metal component, and an inorganic oxide component. Selection of the molecular sieve component allows control over the catalyst performance between ethylbenzene isomerization and ethylbenzene dealkylation depending on overall demand for benzene. Consequently, the molecular sieve may be either a zeolitic aluminosilicate or a non-zeolitic molecular sieve. The zeolitic aluminosilicate (or zeolite) component typically is either a pentasil zeolite, which include the structures of MFI, MEL, MTW, MFS, MTF and FER (IUPAC Commission on Zeolite Nomenclature), MWW, a beta zeolite, or a mordenite. The non-zeolitic molecular sieve is typically one or more of the AEL framework types, especially SAPO-11, or one or more of the ATO framework types, especially MAPSO-31, according to the "Atlas of Zeolite Structure Types" (Butterworth-Heineman, Boston, Mass., 3rd ed. 1992).

The metal component typically is a noble metal component, and may include an optional base metal modifier component in addition to the noble metal or in place of the noble metal. The noble metal is a platinum group metal selected from platinum, palladium, rhodium, ruthenium, osmium, and iridium. The base metal is selected from the group consisting of rhenium, tin, germanium, lead, iron, cobalt, nickel, indium, gallium, zinc, uranium, dysprosium, thallium, and mixtures thereof. The base metal may be combined with another base metal, or with a noble metal. In an embodiment, the total metal in the isomerization catalyst ranges from about 0.01 to about 10 mass-percent, in another embodiment, the amount of metal ranges from about 0.1 to about 3 mass-percent. Suitable zeolite amounts in the catalyst range from about 1 to about 99 mass-percent, and in an embodiment between about 10 to about 90 mass-percent, and between about 25 to about 75 mass-percent in another embodiment. The balance of the catalyst is composed of inorganic oxide binder, typically alumina. In some instances, it may be desirable to modify the catalyst such as by sulfiding either in-situ or ex-situ. One isomerization catalyst for use in the present invention is disclosed in U.S. Pat. No. 4,899,012, the teachings of which are incorporated herein by reference.

Typical isomerization conditions include a temperature in the range from about 0° C. to about 600° C. and a pressure from about 100 kPa to about 6 MPa absolute. The weight hourly hydrocarbon space velocity of the feedstock relative to the weight of catalyst is from about 0.1 to about 30 hr-1. The hydrocarbon contacts the catalyst in mixture with a gaseous hydrogen at a hydrogen-to-hydrocarbon mole ratio of from about 0.5:1 to about 15:1 or more, and in an embodiment from about 0.5 to about 10 H2/HC. If liquid phase conditions are used for isomerization, then typically no hydrogen is added. The isomerization reactor may comprise one or more individual reactors containing catalyst and may be of any suitable type and configuration. The use of a single reaction vessel having a fixed cylindrical bed of catalyst is preferred, but other reaction configurations using moving beds of catalyst or radial flow reactors may be employed if desired.

In the embodiment shown, the isomerate from isomerization zone 126 is passed via line 128 to lights column 130 which serves to remove as a lower boiling fraction, e.g. benzene and lighter components via line 132. A higher boiling $C7^+$ aromatics containing stream is passed from lights column 130 to deheptanizer column 136 via line 134. A toluene fraction is provided by fractional distillation in deheptanizer column 136 and is removed via line 138. A bottoms stream containing $C8^+$ aromatics is passed via line 140 to xylene column 116. Similar to the reaction zone product distillation assembly, a variety of apparatus arrangements may be used to separate the $C8^+$ aromatics stream from the isomerate for recycle to the xylene column. Therefore, the arrangement of columns such as lights column 130 and deheptanizer column 136 used to accomplish this separation is referred to as the isomerate distillation assembly. Thus, the isomerate produced in the xylene isomerization reactor 126 is passed indirectly to the xylene column 116. The fractions comprising benzene and toluene from the isomerate distillation assembly may be passed to other distillation columns within the xylene production facility for further separations.

Returning to xylene column 116, the feed streams to the column, which are the bottoms fraction from toluene column 110 via line 114 and the bottoms fraction from deheptanizer column 136 via line 140, will both contain $C9^+$ aromatics. The former will contain these heavies from the feed, and the latter from the isomerization which typically co-produces heavies. The fractional distillation of xylene column 116 provides one or more higher boiling fractions. As shown, one higher boiling fraction, which contains $C9^+$ aromatics, is discharged from xylene column 116 via line 142. However, within the broad aspects of the invention, the xylene column may be operated to provide at least two higher boiling fractions, one primarily containing C9 and C10 aromatics and some $C11^+$ aromatics, and the other containing a lesser concentration of C9 and C10 aromatics and a greater concentration of $C11^+$ aromatics. The first fraction preferably contains at least about 0.5 mass percent polycyclic aromatics and the second preferably contains at least about 50 mass percent $C11^+$ aromatics. As the separations are rough, little reboiler duty is required as compared to that typically used in a heavies distillation column to remove substantially all $C11^+$ aromatics from the higher boiling fraction from xylene column 116. As shown in an embodiment, at least a portion of $C9^+$ aromatics produced in the xylene column are returned to the reaction zone via line 142. In general, higher concentrations of $C9^+$ aromatics in the transalkylation feed favor the production of xylenes during the transalkylation. The concentration of the $C9^+$ aromatics should not build-up to such a level that undue loads are placed upon the xylene column or that a large purge must be taken. In an embodiment, the concentration of $C9^+$ aromatics in the transalkylation product is less than about 10 mass percent. In an embodiment the transalkylation product comprises less than about 5 mass percent $C9^+$ aromatics and in another embodiment the $C9^+$ aromatics comprise between about 0.01 and about 5 mass percent of the transalkylation product.

Optionally, purging a portion of the $C9^+$ aromatics may be used to prevent their undesired build up. In an embodiment, less than about 50 mass percent of the $C9^+$ aromatics produced in the xylene column are purged. In another embodiment, less than about 20 mass percent of the xylene column $C9^+$ aromatics are purged, and in an embodiment between about 5 and 20 mass percent are purged. Use of a purge stream may be used such that the transalkylation conditions need not be so severe as to consume sufficient polycyclic aromatics to maintain steady-state conditions. The purge may be used in any suitable manner, but is preferably subjected to a distillation to recover at least a portion of the C9+ monocyclic aromatics contained therein as discussed below.

Line 142 provides fluid communication from xylene column 116 to the transalkylation (reaction) zone 144. Whether the feedstock in line 102 contains benzene and/or toluene, additional lighter aromatic (benzene and/or toluene), if desired, may be provided to transalkylation zone reactor 144 via line 146. The lighter aromatic may be obtained from any convenient source, including, but not limited to lines 106, 112, 132, and 138. While the apparatus of FIG. 1 has been described as having, e.g., toluene column 110 and deheptanizer column 136, both to separate toluene from C8+ aromatics, a single column to provide both functions can be used. Other columns performing the same separation may also be combined in like manner. In an embodiment, the isomerate from the outlet of the isomerization zone is passed to the inlet of the reaction zone product distillation assembly for co-processing with the reaction zone product. This embodiment reduces capital costs by eliminating duplicate equipment. In an embodiment not shown, the isomerization zone and reaction zone share a common hydrogen gas circulation system. For example the effluent from the isomerization and transalkylation reactors may flow into two individual or a single combined product separator, with the gas from the one or multiple separators being combined for recycle to the individual reactors in sequence and/or parallel as desired.

As the transalkylation in accordance with the processes of this invention may be operated such that some, but not all, the polycyclic aromatics are converted, it is possible that a build-up of polycyclic aromatics occurs. While steady state conditions may be achieved without the necessity of a purge, the processes of this invention continuously or intermittently remove a portion of the heavier fraction from xylene column 116 in an embodiment to maintain desired polycyclic aromatic concentrations to transalkylation reactor 144. This purge can be taken as a second higher boiling fraction from xylene column 116 as described above, or it may be an aliquot portion of the higher boiling fraction as depicted as line 159.

The purge may be discarded, e.g., used for fuel, or preferably subjected to a fractional distillation in purge column 161. Purge column 161 provides an overhead enriched in C9 and C10 aromatics which can be passed via line 163 to line 142 and then to the transalkylation reactor 144. Some or all of this stream may be recovered via line 164 as a by-product, e.g., for use as a solvent. The bottoms fraction in purge column 161 is enriched in C11+ aromatics and can be discarded and, for instance, used for fuel. Since the purge is only a fraction of the higher boiling fraction of xylene column 116, e.g., often less than about 50, preferably less than about 20, mass percent of the higher boiling fraction, the purge column can be substantially smaller and require less heat duty than a heavies distillation column used to process the entire higher boiling fraction.

Figure 2:
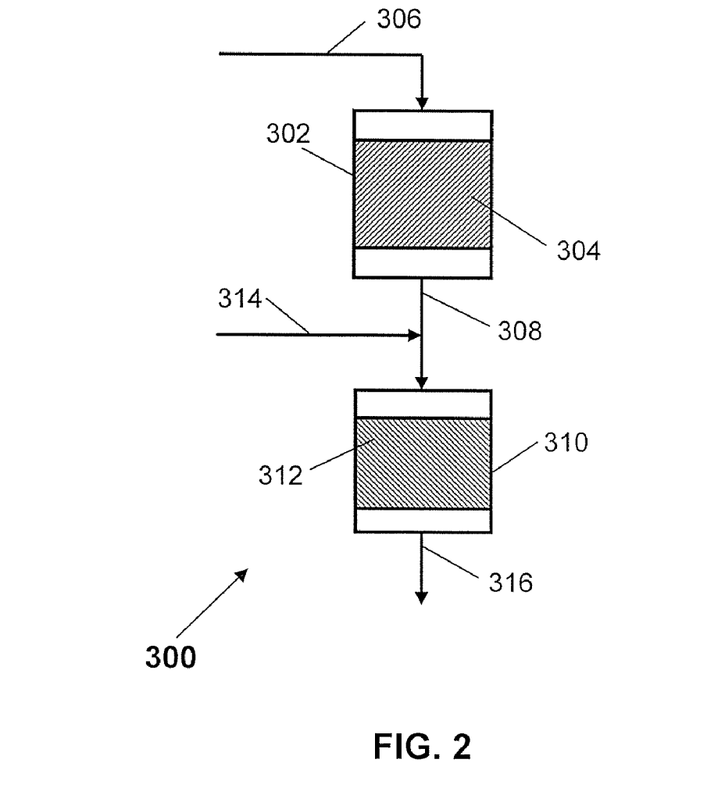
FIG. 2 is a schematic representation of a reactor system having two separate reactor vessels for transalkylation and isomerization.
Figure 3:
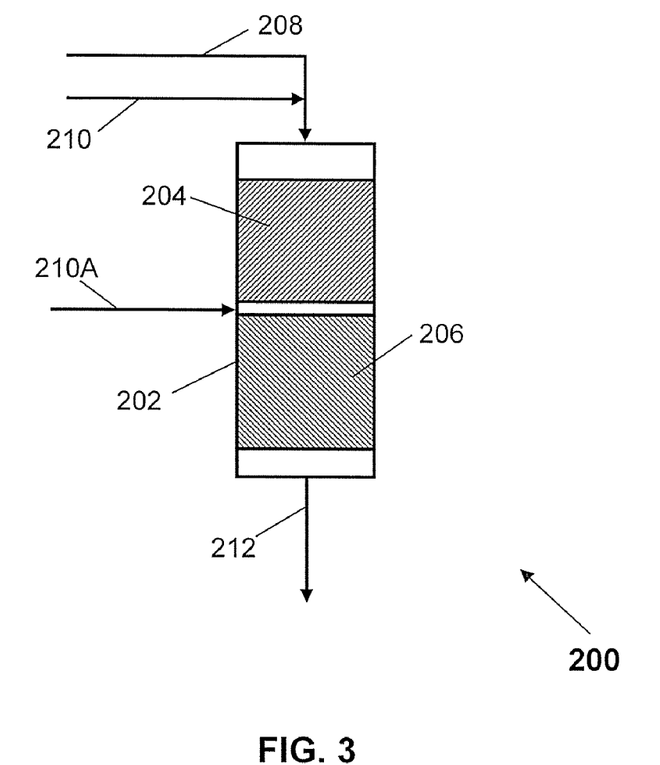
FIG. 3 is a schematic representation of a reactor system having a single reactor vessel having two zones therein for transalkylation and isomerization.

FIGS. 2 and 3 depict various reaction zones comprising integrated transalkylation and xylene isomerization reactor systems. FIG. 3 depicts a reactor system 200 having two zones within a single vessel 202. As shown, vessel 202 contains two distinct catalyst beds, transalkylation catalyst bed 204 and xylene isomerization bed 206. In another embodiment not shown, a single catalyst bed having activity for transalkylation, olefin removal, and xylene isomerization is employed. Feed to reactor vessel 202 is provided by line 208 and one or both of lines 210 and 210A. The feedstock comprising C8 aromatics and olefins from line 102, or from line 162 if an additional fractionation step is used, is provided via line 208 and the higher boiling fraction containing C9+ aromatics from the xylene column is provided via line 210. If additional benzene and/or toluene is fed to catalyst bed 204, one of the illustrated lines, or a separate dedicated line can be used. If desired, all or a portion of the non-equilibrium xylene mixture derived from line 124 can be introduced to catalyst bed 204 via one of the lines illustrated or through a dedicated line, and/or all or a portion of this mixture from line 124 can be introduced between catalyst beds 204 and 206 via line 210A. The isomerate or reaction zone product can be withdrawn via line 212, which equivalent to line 148 is in fluid communication with the reaction zone product distillation assembly.

The system depicted in FIG. 2 generally designated by 300 involves the use of two reactors in sequential flow sequence. Transalkylation reactor 302 has therein catalyst bed 304. Feed to transalkylation reactor 302 is provided by line 306. While one line is shown, it is contemplated that the feed components can be provided by separate lines and the reaction mixture formed within reactor 302. The feed components provided by line 306 are the feedstock from line 102 or line 162 and the higher boiling fraction containing C9+ aromatics from the xylene column. If desired, all or a portion of the non-equilibrium xylene mixture derived from line 124 of FIG. 1 can be introduced into transalkylation reactor 302 via line 306. Line 308 is adapted to direct transalkylation product from reactor 302 to xylene isomerization reactor 310. As shown, line 314 is provided to introduce all or a portion of the non-equilibrium xylene mixture derived from line 124 into xylene isomerization reactor 310. Xylene isomerization reactor contains catalyst bed 312. The isomerate or reaction zone product can be withdrawn via line 316, which equivalent to line 148 is in fluid communication with the reaction zone product distillation assembly.

Thus, the invention enables and encompasses various flow schemes which can take advantage of having the transalkylation zone also remove olefins. In some embodiments, the reaction zone is the transalkylation zone; in other embodiments the reaction zone comprises the transalkylation and isomerization zones either in sequence or combined. In another embodiment not shown, the isomerate in line 128 from an outlet of the isomerization zone is passed to the reaction zone product distillation assembly for separation in combination with the transalkylation product before a portion is recycled to the xylene distillation column. In another embodiment not shown, the reaction zone product distillation assembly comprises a single distillation column having at least one outlet to provide a C8+ aromatic stream to an inlet of the xylene column.

In one embodiment, essentially all of the feedstock to the xylene production facility that is destined for the Xylene Loop is processed in a transalkylation zone to produce xylenes and reduce the olefin content. In some embodiments, one or more portions of the feedstock will not be directed to the Xylene Loop and such portions may, but need not be processed in the transalkylation zone where for example excess benzene, toluene, or other products are exported from the facility. In another embodiment a stream comprising C8 aromatic compounds is obtained from a separate tailored feedstock and/or by separating a feedstock in the feedstock distillation apparatus and passed to the xylene column while the remainder of the feedstock destined for the xylene column is first passed to the transalkylation zone to produce xylenes and reduce the olefins.

Figure 4:
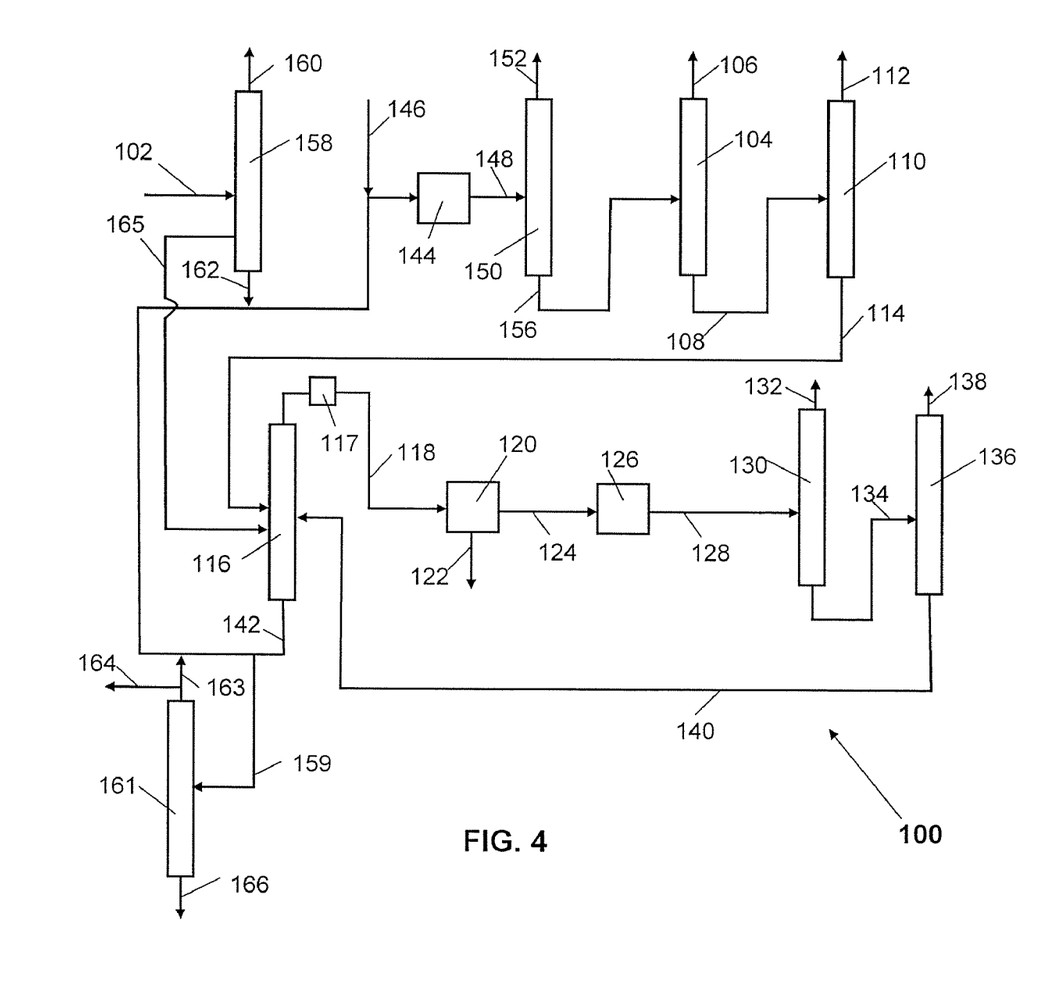
FIG. 4 is a schematic depiction of an apparatus for practicing a process in accordance with this invention.

As illustrated in FIG. 4, a feedstock comprising an olefin and aromatic compounds is passed via conduit 102 to feedstock distillation apparatus 158 which produces a stream comprising an olefin and C9+ aromatic compounds that pass via an outlet and conduits 162 and 142 to reaction zone 144. Feedstock distillation apparatus 158 also produces a stream comprising at least one of benzene and toluene via an outlet and conduit 160 that is passed to reaction zone 144 as desired to increase xylene production and reduce the olefin content. In addition, feedstock distillation apparatus 158 produces a stream comprising C8 aromatic compounds that is passed via an outlet and conduit 165 to xylene column 116. In another embodiment, not illustrated, the feedstock distillation apparatus comprises multiple columns and the stream comprising C8 aromatic compounds is obtained as a column overhead or bottoms stream. Thus, the reaction zone 144 reduces a significant amount of feedstock olefins while producing more xylenes per pass since the transalkylation feed is depleted in xylenes. The portion of the feedstock enriched in C8 aromatic compounds passed via conduit 165 to the xylene column will likely contain olefins. However, the olefin removal capacity required in the xylene production facility is significant reduced by the olefins removed from the other portions of the feedstock which are processed in the transalkylation zone. As before, it is preferred that olefin removal zone 117 be used to process a stream enriched in xylenes as the other aromatic compounds are routed to the transalkylation zone for conversion to xylene and olefin reduction.

The invention claimed is:

1. A process for producing xylene and removing olefins from a feed stream comprising benzene and at least one of an alkyl aromatic compound and an alkyl naphthenic compound, the feed stream having an olefin content as determined by a Bromine Index of at least about 50, said process comprising: contacting the feed stream with a transalkylation catalyst comprising an acidic molecular sieve and at least one metal component having hydrogenation functionality at transalkylation conditions to provide a transalkylation product having an increased concentration of xylene and a reduced olefin content as determined by a Bromine Index at least 60% lower than the Bromine Index of the feed stream.

2. The process of claim 1 wherein the feed stream further comprises at least one of toluene and C9+ aromatics.

3. The process of claim 1 wherein the feed stream has an End Boiling Point of at least about 190° C.

4. The process of claim 1 wherein a net production of methane is not more than about 0.5 mass percent.

5. The process of claim 1 wherein the Bromine Index of the transalkylation product is at least 80% lower than the Bromine Index of the feed stream.

6. The process of claim 1 wherein the Bromine Index of the feed stream is at least about 100.

7. The process of claim 1 wherein less than about 35 mass percent of the total aromatics in the feed are xylenes.

8. The process of claim 1 wherein a Ring Loss is less than about 2 mole percent based upon the moles of monocyclic aromatics in the feed stream.

9. The process of claim 1 wherein the metal component of the transalkylation catalyst comprises at least one of platinum, palladium, rhodium, ruthenium, osmium, iridium, rhenium, tin, germanium, lead, iron, cobalt, nickel, indium, gallium, zinc, uranium, dysprosium, and thallium.

10. The process of claim 9 wherein the metal component comprises rhenium.

11. The process of claim 9 wherein the metal component comprises platinum and tin.

12. The process of claim 9 wherein the metal component is present in an amount to provide a rate of deactivation of the catalyst less than 200 percent as determined under Evaluation Conditions.

13. The process of claim 9 wherein the acidic molecular sieve comprises at least one of BEA, MTW, FAU, MOR, LTL, ITH, ITW, MEL, FER, TON, IWW, MFI, EUO, MTT, HEU, MFS, CHA, ERI, and LTA.

14. The process of claim 13 wherein the acidic molecular sieve comprises at least one of MOR and MFI.

15. A process for producing xylene and removing olefins from a feedstock comprising C8 aromatics the feedstock having an olefin content as determined by a Bromine Index of at least about 100, said process comprising:
(a) mixing said feedstock and a stream comprising C9+ aromatics, to provide a mixture, said mixture having a Bromine Index of at least about 50 and an End Boiling Point of at least about 210° C.; and
(b) contacting the mixture with a transalkylation catalyst comprising an acidic molecular sieve and at least one metal component having hydrogenation functionality at transalkylation conditions to provide a transalkylation product having an increased concentration of xylenes and a reduced olefin content as determined by a Bromine Index at least 60% lower than the Bromine Index of the mixture.

16. The process of claim 15 wherein said mixture further comprises at least one of benzene and toluene, and the ratio of total moles of benzene and toluene to total moles of C9+ aromatics is greater than about 0.01:1.

17. The process of claim 15 wherein between about 20 and about 75 mole percent of the total C9+ aromatics in the mixture are converted in step (b).

18. The process of claim 15 wherein the mass ratio of said feedstock to said stream comprising C9+ aromatics in the mixture is between about 0.01:1 to about 3:1.

19. The process of claim 15 wherein the End Boiling Point of the transalkylation product is at least 10° C. lower than that of the mixture.

* * * * *